United States Patent [19]

Naegeli

[11] 3,932,517

[45] Jan. 13, 1976

[54] ISOPROPYL-(3-OXOPENTENYL)-CYCLOPENTENES

[75] Inventor: Peter Naegeli, Wettingen, Switzerland

[73] Assignee: Givaudan Corporation, Clifton, N.J.

[22] Filed: Nov. 7, 1973

[21] Appl. No.: 413,470

[30] Foreign Application Priority Data
Nov. 15, 1972  Switzerland.................... 16605/72

[52] U.S. Cl. ......... 260/586 R; 252/522; 260/586 P; 260/598; 260/617 R; 260/617 E
[51] Int. Cl.² ........................................ C07C 49/61
[58] Field of Search ............................... 260/586 R

[56] References Cited
UNITED STATES PATENTS
3,285,950   11/1966   Weber ............................... 260/586

OTHER PUBLICATIONS

Wohnsky et al., *J. Org. Chem.*, Vol. 29, pp. 3740–3742, (1964).
Berlstein, *Org. Chem.*, Vol. VII, P. 647, III Supplement (1958).

*Primary Examiner*—Norman Morgenstern
*Attorney, Agent, or Firm*—Thomas Cifelli, Jr.

[57] ABSTRACT

Novel cyclopentene derivatives, a process for making same and odorant compositions containing the novel compounds are disclosed.

5 Claims, No Drawings

ISOPROPYL-(3-OXOPENTENYL)-CYCLOPENTENES

FIELD OF THE INVENTION

This invention relates to the fields of new chemicals and odorant compositions.

SUMMARY OF THE INVENTION

The cyclopentene derivatives provided by this invention have the following general formula

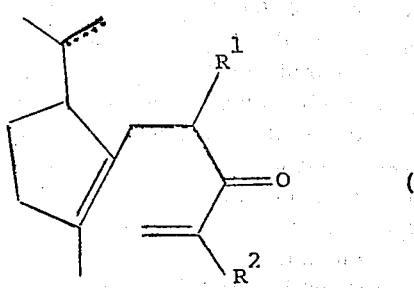 (I)

wherein $R^1$ and $R^2$ each independently represent a hydrogen atom or a lower alkyl group and the broken line denotes an optional bond.

The term "lower alkyl" is used in this description and in the accompanying claims to mean a straight-chain or branched-chain group containing 1–6 carbon atoms (e.g. methyl, ethyl, propyl, isopropyl or tert.butyl). A preferred lower alkyl group is the methyl group.

According to the process provided by this invention, the cyclopentene derivatives of formula I are manufactured by oxidising a compound of the general formula

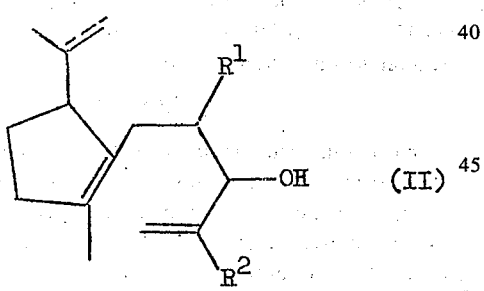 (II)

wherein $R^1$, $R^2$ and the broken line have the significance given earlier.

DESCRIPTION OF THE PREFERRED EMBODIMENTS

The oxidation can be carried out in a manner known per se according to methods which are generally known for the oxidation of allylic hydroxy groups. Examples of oxidising agents which can be used are chromic acid (in its various forms such as, for example, Jones reagent), activated manganese dioxide, $SO_3$ (preferably as the pyridine complex in the presence of dimethyl sulphoxide and triethylamine), silver oxide or silver carbonate in the presence of diatomaceous earth. The working up of the oxidation mixture as well as the purification of the cyclopentene derivatives of formula I can be carried out according to customary methods.

The starting materials of formula II can be prepared in a manner known per se from a compound of the general formula

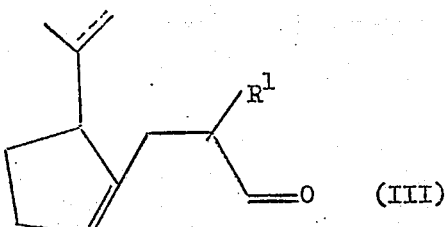 (III)

wherein $R^1$ and the broken line have the significance given earlier, by reaction with an organometallic compound, especially with an alkali metal acetylide or with a Grignard compound of the general formula

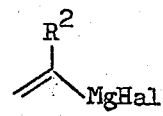

wherein $R^2$ has the significance given earlier and Hal represents a chlorine or bromine atom.

When a compound of formula III is reacted with an acetylide it is necessary to catalytically partially hydrogenate the initially obtained compound of the general formula

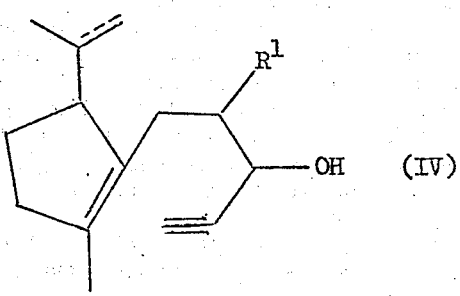 (IV)

wherein $R^1$ and the broken line have the significance given earlier, in a manner known per se; for example, in the presence of a Lindlar catalyst ($Pd/CaCO_3$ deactivated with PbO).

Insofar as they are not known, the compounds of formula III can be prepared, for example, by reacting 3-isopropenyl-1-methyl-2-methylene-cyclopentan-1-ol with a vinylether of the general formula

 (V)

wherein $R^1$ has the significance given earlier and R represents an alkyl group, and, if desired, hydrogenating a resulting 3-isopropenyl-cyclopentene of the general formula

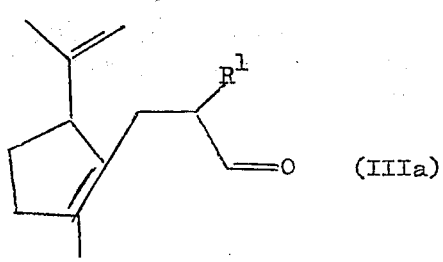

(IIIa)

wherein R[1] has the significance given earlier, to give the corresponding 3-isopropyl compound.

The cyclopentene derivatives of formula I possess particular fragrance properties, especially in the foreground is a woody basic note. They can accordingly be used as odorants in perfumery; for example, in the manufacture or for the modification of the fragrance of odorant compositions such as perfumes, perfume bases, etc by addition of olfactory perceptible amounts (e.g. 0.1–10 wt %) to mixtures of known odorants. The cyclopentene derivatives of formula I can be used alone or in the form of odorant compositions for the perfuming of technical and cosmetic products of all types; for example, of solid and liquid detergents, synthetic washing agents, aerosols, soaps, creams, lotions, etc in concentrations of, for example, about 0.001–0.1 wt %. They can also be used as starting materials for the manufacture of other odorants.

The following Examples illustrate the process provided by the present invention:

EXAMPLE 1

A solution of 2.1 g of 2-(3-hydroxy-4-pentenyl)-3-isopropyl-1-methyl-1-cyclopentene in 100 ml of acetone was treated at −10°C with 4 ml of Jones reagent. After 2 minutes, the solution was poured into an ice-cold 2-N soda solution and the mixture extracted with ether. The extract was worked up in the usual manner and yielded 2 g of a yellowish oil which, after distillation under reduced pressure, gave 1.6 g of pure 3-isopropyl-1-methyl-2-(3-oxo-4-pentenyl)-1-cyclopentene; b.p. $_{0.01}$ = 65°C;

IR (film): $\nu$ = 1700/1685, 1620, 1470, 1402, 1385, 1365, 1185, 1100, 990, 965 cm$^{-1}$. Odor: woody, ketone-like.

EXAMPLE 2

In a manner analogous to that described in Example 1, from 2-(3-hydroxy-4-methyl-4-pentenyl)-3-isopropyl-1-methyl-1-cyclopentene there was prepared 3-isopropyl-1-methyl-2-(4-methyl-3-oxo-4-pentenyl)-1-cyclopentene; b.p. $_{0.01}$ = 80°C;

UV (cyclohexane): $\Lambda_{max}$ = 214 nm ($\epsilon$ = 9000); IR (film): $\nu$ = 1680, 1635, 1465/55, 1385, 1365, 1090, 935 cm$^{-1}$. Odor: woody, ionone-like, sweet, fig-like, somewhat fruity.

EXAMPLE 3

In a manner analogous to that described in Example 1, from 2-(3-hydroxy-2-methyl-4-pentenyl)-3-isopropyl-1-methyl-1-cyclopentene there was prepared 3-isopropyl-1-methyl-2-(2-methyl-3-oxo-4-pentenyl)-1-cyclopentene; b.p. $_{0.005}$ = 78°C;

UV (cyclohexane): $\Lambda_{max}$ = 212 nm ($\kappa$ = 8400); IR (film): $\nu$ = 1700, 1680, 1615, 1460, 1400, 1385, 1365, 1030, 985/975 cm$^{-1}$. Odor: fresh, woody, spicy.

EXAMPLE 4

In a manner analogous to that described in Example 1, from 2-(3-hydroxy-2,4-dimethyl-4-pentenyl)-3-isopropyl-1-methyl-1-cyclopentene there was prepared 3-isopropyl-1-methyl-2-(2,4-dimethyl-3-oxo-4-pentenyl)-1-cyclopentene; b.p. $_{0.01}$ = 90°C;

UV (cyclohexane): $\Lambda_{max}$ = 212 nm ($\epsilon$ = 7900); IR (film): $\nu$ = 1680, 1630, 1460, 1380, 1370, 930 cm$^{-1}$. Odor: woody, cedar-like, fresh.

EXAMPLE 5

A solution of 20 g of 2-(3-hydroxy-4-pentenyl)-3-isopropenyl-1-methyl-1-cyclopentene in 1000 ml of acetone was mixed with 40 ml of Jones reagent with stirring at −10°C within 20 minutes. The mixture was stirred for a further 5 minutes at −5°C, poured into an excess of ice-cold 2-N soda solution and extracted with ether. The extract was worked up in the usual manner and yielded 18.5 g of a bright yellow oil which, after distillation under reduced pressure, gave 16 g of pure 3-isopropenyl-1-methyl-2-(3-oxo-4-pentenyl)-1-cyclopentene; b.p. $_{0.001}$ 48°C;

IR (film): $\nu$ = 3100, 1700/1685, 1645, 1620, 1442, 1402, 1375, 1100, 990, 968, 895 cm$^{-1}$. Odor: pleasant floral-ester-like, geranium-like, linalool-like.

EXAMPLE 6

In a manner analogous to that described in Example 5, from 2-(3-hydroxy-2-methyl-4-pentenyl)-3-isopropenyl-1-methyl-1-cyclopentene there was prepared 3-isopropenyl-1-methyl-2-(2-methyl-3-oxo-4-pentenyl)-1-cyclopentene; b.p. $_{0.02}$ = 84°C;

UV (cyclohexane): $\Lambda_{max}$ = 213 nm ($\epsilon$ = 9500); IR (film): $\nu$ = 3100, 1702, 1682, 1645, 1615, 1455/40, 1405, 1375, 1030, 990, 975, 892 cm$^{-1}$. Odor: fatty, similar to undecylenic acid.

EXAMPLE 7

In a manner analogous to that described in Example 5, from 2-(3-hydroxy-4-methyl-4-pentenyl)-3-isopropenyl-1-methyl-1-cyclopentene there was prepared 3-isopropenyl-1-methyl-2-(4-methyl-3-oxo-4-pentenyl)-1-cyclopentene; b.p. $_{0.01}$ = 88°C;

UV (cyclohexane); $\Lambda_{max}$ = 213 nm ($\epsilon$ = 9900); IR (film): $\nu$ = 3110, 1680, 1645, 1450, 1375, 1090, 935, 895 cm$^{-1}$. Odor: fresh, woody, cedar-like, green.

EXAMPLE 8

In a manner analogous to that described in Example 5, from 2-(3-hydroxy-2,4-dimethyl-4-pentenyl)-3-isopropenyl-1-methyl-1-cyclopentene there was prepared 3-isopropenyl-1-methyl-2-(2,4-dimethyl-3-oxo-4-pentenyl)-1-cyclopentene; b.p. $_{0.01}$ = 92°C;

UV (cyclohexane): $\Lambda_{max}$ = 216 nm ($\epsilon$ = 8800) IR (film): $\nu$ = 3110, 1680, 1645, 1455, 1375, 935, 895 cm$^{-1}$. Odor: woody, cedar-like, camphoraceous.

The following Examples illustrate odorant compositions containing the cyclopentene derivatives provided by the invention.

EXAMPLE A

Odorant composition containing 3-isopropenyl-1-methyl-2-(3-oxo-4-pentenyl)-1-cyclopentene.

| | Parts by weight |
|---|---|
| Phenylethyl alcohol | 400 |
| Linalool | 30 |
| Geranyl acetate | 20 |
| Eugenol | 10 |
| Nonylaldehyde (1% in phthalic acid diethyl ester) | 10 |
| Nerol | 50 |
| Citral | 5 |
| 6-Methylionone | 15 |
| Rhodionol 70 Givaudan (Rhodinol/Citronellol in ratio of 70/30) | 80 |
| Citronellol | 180 |
| Baccartol Givaudan (condensation product of citronella oilacetone) | 100 |
| 3-Isopropenyl-1-methyl-2-(3-oxo-4-pentenyl)-1-cyclopentene | 100 |
| | 1000 |

By the addition of 3-isopropenyl-1-methyl-2-(3-oxo-4-pentenyl)-1-cyclopentene, the rose-like note of the composition is intensified.

EXAMPLE B

Odorant composition containing 3-isopropyl-1-methyl-2-(4-methyl-3-oxo-4-pentenyl)-1-cyclopentene.

| | Parts by weight |
|---|---|
| Bergamot oil | 200 |
| Oak moss soluble | 60 |
| Vetiveryl acetate | 40 |
| Eugenol | 40 |
| Lavandin | 80 |
| Lavender oil | 100 |
| Sandalwood oil | 100 |
| Cedryl acetate | 120 |
| Musk ambrette | 100 |
| Lemon oil Italian | 40 |
| Sauge sclaree 20 | |
| Orange oil Californian | 20 |
| Thyme oil white | 20 |
| 3-Isopropyl-1-methyl-2-(4-methyl-3-oxo-4-pentenyl)-1-cyclopentene | 60 |
| | 1000 |

By the addition of 3-isopropyl-1-methyl-2-(4-methyl-3-oxo-4-pentenyl)-1-cyclopentene, the fresh, lavender-like note of the composition is emphasised.

What we claim is:
1. Cyclopentene derivatives of the general formula

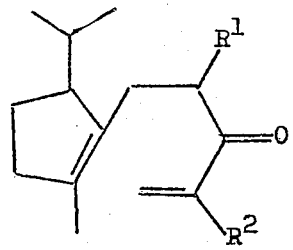

wherein $R^1$ and $R^2$ each independently represent a hydrogen atom or a lower alkyl group.

2. 3-Isopropyl-1-methyl-2-(3-oxo-4-pentenyl)-1-cyclopentene.

3. 3-Isopropyl-1-methyl-2-(4-methyl-3-oxo-4-pentenyl)-1-cyclopentene.

4. 3-Isopropyl-1-methyl-2-(2-methyl-3-oxo-4-pentenyl)-1-cyclopentene.

5. 3-Isopropyl-1-methyl-2-(2,4-dimethyl-3-oxo-4-pentenyl)-1-cyclopentene.

* * * * *